United States Patent [19]

Kane et al.

[11] 4,179,468
[45] Dec. 18, 1979

[54] CYCLIC TERPENOID ONIUM SALTS, THEIR PREPARATION AND USES

[75] Inventors: Bernard J. Kane, Atlantic Beach; Richard A. Von Genk, Jacksonville, both of Fla.

[73] Assignee: SCM Corporation, Cleveland, Ohio

[21] Appl. No.: 916,966

[22] Filed: Jun. 19, 1978

[51] Int. Cl.² .............................................. C07C 87/68
[52] U.S. Cl. ...................... 260/567.6 M; 260/606.5 F; 568/828; 568/822; 585/357; 585/358; 585/359
[58] Field of Search ................ 260/567.6 M, 606.5 F, 260/675.5; 568/824, 875, 822, 826, 828

[56] References Cited

U.S. PATENT DOCUMENTS

| 3,714,270 | 1/1973 | Fenton | 568/822 |
| 3,932,539 | 1/1976 | Kane et al. | 260/567.6 M |

OTHER PUBLICATIONS

Brown, Tetrahedron, vol. 12, pp. 117-138 (1961).
Mori et al., Tetrahedron, vol. 26, pp. 2815-2819 (1970).

Primary Examiner—James H. Reamer
Attorney, Agent, or Firm—Merton M. Douthitt; Gordon P. Becker

[57] ABSTRACT

Acyclic terpenoid onium salts are cyclized in an acidic aqueous solution at a temperature of at least about 80° C.

23 Claims, No Drawings

CYCLIC TERPENOID ONIUM SALTS, THEIR PREPARATION AND USES

CROSS-REFERENCE TO RELATED APPLICATIONS

This application is cross-referenced to applicant's commonly assigned copending application Ser. No. 860,284, filed on Dec. 14, 1977, entitled CYCLIC TERPENOID AMINES, THEIR PREPARATION AND USES. The disclosure of said application is expressly incorporated herein by reference.

BACKGROUND OF THE INVENTION

This invention relates to certain novel cyclic terpenoid onium salts, their preparation and their uses.

While preparing unsaturated terpene alcohols according to the Kane and Von Genk process (U.S. Pat. No. 3,932,539), it was discovered unexpectedly that terpenoid quaternary ammonium salts subjected to the hydration step of such process were cyclized rather than hydrated when such hydration step was practiced at higher temperatures of above about 80° C. and advantageously above about 100° C. Subsequently, the discovery was broadened to include onium salts selected from quaternary ammonium salts and phosphonium salts. The novel cycloterpenoid onium salts disclosed herein are useful in the synthesis of fragrances and carotenoids, for example. The wide variety of uses for the instant cycloterpenoid onium salts will be delineated further in this application.

BROAD STATEMENT OF THE INVENTION

The present invention is a process for cyclizing an acyclic terpenoid group of an onium salt selected from a quaternary ammonium salt and a phosphonium salt, where the terpenoid group is a neryl group or a geranyl group. Such process comprises maintaining an acidic aqueous mixture of the onium salt at a temperature of at least about 80° C. until said acyclic terpenoid group cyclizes. In the aqueous solution there is at least about 1.1 equivalents of acid per equivalent of the onium salt for accomplishing the cyclization.

DETAILED DESCRIPTION OF THE INVENTION

The feed for the present process is an acyclic terpenoid onium salt. Preferably, the onium salt is a quaternary ammonium salt, although phosphonium salts may be useful in the process also.

Acyclic terpenoid quaternary ammonium salts may be prepared by a variety of techniques well known in the art. One method involves the reaction of a neryl/geranyl halide with a tertiary amine, such as is shown in U.S. Pat. No. 3,932,539, the disclosure of which is expressly incorporated herein by reference. This reaction can be represented conventionally as follows:

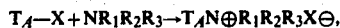

where
$T_A$ is a neryl or geranyl group;
X is Cl, Br, or I;
$R_1R_2R_3$ independently are $C_{1-4}$ alkyl groups;
$R_1R_2$ independently are $C_{1-4}$ alkyl groups and $R_3$ is a $C_{6-7}$ cycloalkyl, aralkyl, or aryl group; or
$R_1$ is a $C_{1-4}$ alkyl group, and $R_2R_3$ are a heterocyclic residue.

This reaction preferably is conducted with about 1.01 to 2.0, preferably 1.1 to 1.2, moles of tertiary amine per mole of acylic terpenoid halide at a reaction temperature of from about −20° C. to 100° C., preferably 20° to 60° C. In this reaction, the reactivity of the amine with the terpene chloride will depend upon electronic considerations and steric considerations. Some amines, particularly those connected to an aromatic system, eg. N,N-dimethylaniline, are less readily alkylated by the terpene chloride than are aliphatic or benzylic amines. Also, rather large and bulky groups attached to the amine can be expected to sterically hinder the alkylation of the amine by the terpene chloride. One such unreactive, sterically hindered amine for this alkylation reaction is ethyldiisopropylamine. The starting amine, then, to be useful, must be alkylated at a reasonable rate by the neryl/geranyl chloride.

Alternatively, the acrylic terpenoid tertiary amine can be prepared first and then converted to the quaternary ammonium salt by the addition of an alkyl halide, alkyl sulfate or the like. The acyclic terpenoid amines may be prepared as shown in applicants' co-pending application Ser. No. 860,284. One method shown in such application is the alkylation of a neryl/geranyl halide by a secondary amine. Alternatively, a secondary amine, such as diethylamine or the like, can be added directly to myrcene in the presence of special catalysts such as sodium naphthalenide according to the process proposed by Watanabe et al in the *Australian Journal of Chemistry*, 1974, Volume 27, pages 531-535. Also, N,N-diethylnerylamine may be prepared by the telomerization of isoprene with diethylamine in the presence of n-butyllithium catalyst according to the process of Takabe et al, *Tetrahedron Letters*. No. 34, pages 3005-3006 (1975). Geranyl/nerylamines may be prepared additionally by the reduction of citral oxime as taught in U.S. Pat. No. 4,017,634, or by the Gabriel synthesis as described in the *Journal of Organic Chemistry*, 1972, Volume 37, pages 4036-4039. The disclosures of all of the foregoing references are incorporated expressly herein by reference.

The acyclic terpenoid amines conversion into the corresponding quaternary ammonium salt can be represented conventionally as follows:

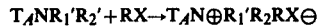

where
$T_A$ is defined above;
X is a monovalent anion such as halogen, nitrate, acetate, hydroxide or the like, but preferably Cl, Br, or I;
R is an alkyl group, preferably a $C_{1-4}$ alkyl group;
$R_1'$ is a $C_{1-4}$ aliphatic group, preferably a $C_{1-4}$ alkyl group; and
$R_2'$ is a monovalent group, usually a monovalent organic group, and advantageously a $C_{1-4}$ alkyl group; or
$R_1'R_2'$ are joined as a heterocyclic residue.

Phosphonium salt preparations generally are analogous to those preparations used for the quaternary ammonium salts. Thus, neryl/geranyl halides may be reacted with triphenylphosphine, for example. Representative onium salts which can be subjected to the instant cyclization process include, for example, neryl/geranyl triethylammonium chloride, neryl/geranyl-methylmorpholinium chloride, neryl/geranyl triphenyl phosphonium chloride, neryl/geranyl trimethylammonium chloride, and the like.

Regardless of how the acyclic terpenoid onium salts are prepared, cyclization is practiced by maintaining an acidic aqueous mixture of the onium salt until cyclization occurs. At least about 1.1 equivalents of acid per equivalent of said onium salt is used in this reaction, advantageously at least about 2 equivalents of acid, and preferably about 2 to 3 equivalents of the acid. While more than 3 equivalents of the acid can be used, such amounts tend to be less convenient to handle and more costly to use. Typically, about a 20% to 30% acid concentration in the aqueous mixture will be found to be useful for the instant cyclization reaction. Appropriate acids for this reaction include, for example, hydrochloric acid, sulfuric acid, phosphoric acid, hydrobromic acid, and the like. The cyclization reaction preferably is carried at a temperature above about 80° C., and usually between about 80° and 120° C., preferably under reflux conditions. Temperatures higher than 120° C. can be practiced and are advantageous for faster reaction rates; however, this would require use of pressurized equipment for conducting the reaction. Temperatures of about 100° to 120° are quite useful when a 20% to 30% acid concentration is maintained in the reaction solution. Inert solvents such as ethers, cellosolves, and the like can be used as is necessary, desirable or convenient.

The progress of the cyclization reaction can be followed in an indirect manner since the onium salt compounds are not volatile and, hence, cannot be analyzed by conventional gas chromatography. A convenient indirect manner for following the cyclization of neryl/geranyl quaternary ammonium salts involves taking samples of the aqueous reaction mixture and rendering them strongly basic, followed by heating to decompose the quaternary ammonium hydroxide (a Hoffmann elimination) to form olefins related to the structure of the quaternary ammonium salt in the reaction mixture. Alternatively, one may use a basic ion exchange resin or treatment with silver hydroxide followed by thermal decomposition for this olefin formation. The liberated olefins then are analyzed by gas chromatography. The extent to which cyclization has occurred is measured in terms of the ratio of the uncyclized olefin (myrcene) to the cyclized olefins (gamma and delta pyronenes). Similar techniques can be used to follow the progress of the cyclization reaction for phosphonium salts except that the corresponding products are cyclized and uncyclized hydrolysis products.

Gamma- and delta-pyronenes can be represented conventionally by the following general structures:

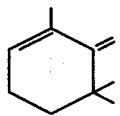
gamma-pyronene

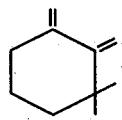
delta-pyronene

The product of cyclogeranyl ammonium salts made by the instant process are useful for their bacteriocidal properties. Additionally, the cyclogeranyl quaternary ammonium hydroxides can be thermally decomposed to form gamma- and delta-pyronenes by a conventional Hoffman elimination or degradation process. A limited report on this reaction was given by Mori et al in *Tetrahedron*, Vol. 26, pages 2815–2819 (1970), the disclosure of which is expressly incorporated herein by reference. It should be noted that in addition to the gamma- and delta-pyronenes made by the decomposition of the cyclogeranyl quarternary ammonium salts, lesser amounts of beta-cyclogeraniol and cyclolinalool (1,3,3-trimethyl-2-methylene-1-cyclohexanol) may result also (see Example III).

Gamma- and delta-pyronenes are valuable compounds in the synthesis of alcohols used in perfumery and in a wide variety of other reactions. For instance, gamma-pyronene is reported to be useful for the synthesis of thujopsene according to Mori et al as cited above. Additionally, gamma-pyronene is reported to be useful in the synthesis of a $C_{11}$ intermediate for the production of Vitamin A and carotenoids as reported in German Pat. No. 1,025,871. Also, gamma-pyronene can be converted into α-cyclogeraniol, a useful perfumery ingredient, by a conventional hydroboration process typically used for making alcohols. Such hydroboration process comprises reacting the gamma-pyronene with diborane ($B_2H_6$) in diglyme at about 25° C. followed by oxidation with an aqueous alkaline solution of hydrogen peroxide at a temperature of between about 35° to 40° C. See the following references for good discussions of hydroboration: *HYDROBORATION*, W. A. Benjamin, Inc., N.Y., N.Y. (1962); *Organic Reactions*, Vol. 13, pp. 1–54, John Wiley & Sons, N.Y., N.Y. (1963); and Brown, *Tetrahedron Letters*. Vol. 12, pp. 117–138 (1961), the disclosures of which are incorporated expressly herein by reference. In addition to conducting the hydroboration process with diborane in diglyme, one may also use sodium borohydride with $BF_3$ etherate in diglyme, diborane in tetrahydrofuran or ethyl ether, lithium aluminum hydride with $BF_3$ etherate in ethyl ether, lithium borohydride with $BF_3$ etherate in tetrahydrofuran or ethyl ether containing 10% zinc chloride, lithium borohydride with $BF_3$ etherate in tetrahydrofuran, sodium borohydride with boron trichloride in diglyme, and the like. Reaction temperatures using the above ingredients typically range from about 0° to 25° C. The oxidation reaction of the terpene borane intermediate generally is conducted at reaction temperatures of about 0° to 40° C. and higher.

Delta-pyronene can be converted to the alcohols 1-hydroxymethyl-2-methylene-3,3-dimethylcyclohexane and "gamma-cyclogeraniol" by similar hydroboration process. These novel alcohols can be represented conventionally as follows:

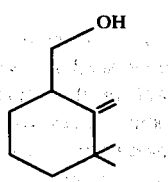
1-hydroxymethyl-2-methylene 3,3-dimethylcyclohexane

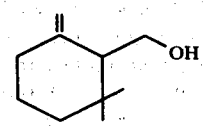
1-methylene-2-hydroxymethyl-3,3-dimethylcyclohexane (gamma-cyclogeraniol)

Gamma-cyclogeraniol can be used for the synthesis of (+)-diumycinol according to a process reported by Grieco et al in the *Journal of Organic Chem.*, Vol. 40, No. 15, pages 2261–2263 (1975). The 1-hydroxymethyl-2-methylene-3,3-dimethylcyclohexane is useful for its fragrance.

Delta-pyronene also can be useful in synthesizing certain Diels-Alder compounds reported in U.S. Pat. No. 3,076,022. These olefactory compounds may be prepared by reacting delta-pyronene (as the diene) with methyl isopropenyl ketone (as the dienophile) according to the conventional Diels-Alder reaction. The following typifies this reaction for illustrative purposes:

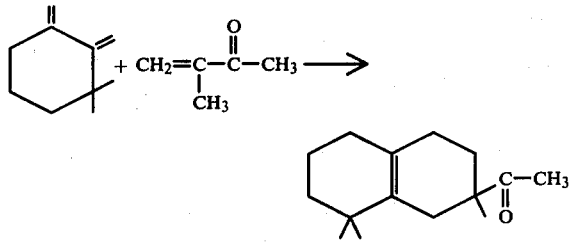

Certain of the β-cyclogeranyl phosphonium salts are valuable in the synthesis of Vitamin A and Vitamin A-related compounds according to Pommer in *Angew. Chem. Internat. Edition/Issue*, pages 31–40 (1960).

The following examples show in detail how the present invention can be practiced but should not be construed as limiting. In this application, all temperatures are in degrees Centigrade, all percentages are weight percentages, unless otherwise expressly indicated. Also, all references cited herein are expressly incorporated herein by reference.

EXAMPLE I

Preparation of Cyclogeranyl Trimethylammonium Chloride

Gaseous trimethylamine, 525 grams, was added to 2,000 grams of myrcene hydrochloride at a reaction temperature of 25°–30° C. with removal of the heat of reaction being provided for. The reaction was conducted for about 6 hours. Two thousand grams of water were added to the reaction mixture to dissolve the geranyl trimethylammonium chloride salt. The water layer was washed two times with 300 milliliters of heptane each time to remove the terpene byproducts. The weight of the washed solution was 3,852 grams. This solution of geranyl trimethylammonium chloride then was refluxed for 18 hours with a solution of 3,068 grams of 15% hydrochloric acid in order to cyclize the geranyl trimethylammonium chloride salt.

EXAMPLE II

Conversion of β-Cyclogeranyltrimethylammonium Chloride to Gamma- and Delta-Pyronenes The cyclogeranyl trimethyl ammonium chloride product solution of Example I was added gradually to a refluxing solution of 14,602 grams of water and 7,618 grams of sodium hydroxide. This reaction procedure produces the corresponding cyclogeranyl trimethylammonium hydroxides which are decomposed at the reaction temperature of 120°–125° C. to produce gamma- and delta-pyronenes. The formed pyronenes were removed from the reaction mixture as a distillate. Aqueous distillate from the reaction mixture was returned to the pot as needed in order to maintain the reaction temperature in the range of 120°–125° C.

The total weight of pyronenes distilled from the reaction mixture was 794 grams. Gas chromatographic analysis indicated that the pyronenes were a mixture by weight of approximately 64% gamma-pyronene and 36% delta-pyronene. These two pyronenes separate readily by fractional distillation as the gamma-isomer boils at about 103° C. and the delta-isomer at 91° C. at a total pressure of 100 mm of Hg.

EXAMPLE III

Conversion of β-Cyclogeranyl Trimethylammonium Iodide to gamma-Pyronene and delta-Pyronene The β-cyclogeranyl trimethylammonium iodide was prepared by refluxing 4 grams of β-cyclogeranyldimethylamine (about 95% purity) with excess methyl iodide for 48 hours.

The β-cyclogeranyl trimethylammonium iodide was dispersed in 200 cc of hot water to which was added 100 grams of sodium hydroxide. This solution was cohobated at about 125° C. to yield 2.5 grams of oil. This oil analyzed by gas chromatography to contain 17.6% delta-pyronene, 65.9% gamma-pyronene, 4% "cyclolinalool", and 1.08% β-cyclogeraniol.

EXAMPLE IV

Conversion of gamma-Pyronene to α-Cyclogeraniol

Sodium borohydride, 2.3 grams, was added to a solution of 27.2 grams gamma-pyronene in 100 milliliters diglyme, bis(2-methoxyethyl)ether, and to this slurry was added 10.1 milliliters of boron trifluoride etherate in 15 milliliters diglyme solution. The boron trifluoride etherate was added over a 30 minute interval and the reaction temperature was held at 25° C. The reaction mixture then was washed with 20 milliliters of water, followed by a wash with 22 milliliters of 3N sodium hydroxide solution. The terpene boron intermediate then was oxidized by the addition of 22 milliliters of 30% hydrogen peroxide over a 15–20 minute interval at 30°–40° C.

The reaction mixture was extracted with ether solvent and this extract washed several times with water. After removal of the solvent, the crude product was distilled to isolate high purity α-cyclogeraniol (boiling point of 94° C. at 10 mm of Hg). NMR (nuclear magnetic resonance) analysis confirmed the structure of the α-cyclogeraniol product.

EXAMPLE V

Conversion of delta-Pyronene into 1-Methylene-2-hydroxymethyl-3,3-dimethylcyclohexane and 1-Hydroxymethyl-2-methylene-3,3-dimethylcyclohexane Delta-Pyronene (27.2 g.) in 100 ml diglyme was stirred at 25° C. with 2.3 g. NaBH$_4$, and a solution of 10.1 ml BF$_3$ etherate in 16 ml diglyme was added thereto over a period of 30 minutes. After completion of the addition, the reaction mixture was stirred for 1 hour at 25° after which excess hydride was decomposed with 20 ml H$_2$O. Sodium hydroxide (22 ml of 13% solution) then was added followed by the addition of 20 ml of 30% H$_2$O$_2$ over a 20–30 minute period. This mixture was stirred for 1 hour at 25°–30°. Workup of this mixture involved extraction with 150 ml ether and washing with 10% NaCl solution. Solvent removal under reduced pressure provided 30 g of crude product which was fractionated at 10 mm on a Nester-Faust spinning band column to give 6.7 g pure 1-methylene-2-hydroxymethyl-3,3-dimethylcyclohexane (gamma-cyclogeraniol) and 4.0 g of 90–95% pure 1-hydroxymethyl-2-methylene-3,3-dimethylcyclohexane.

EXAMPLE VI

Preparation of beta-Cyclogeranyl Triphenylphosphonium Chloride

Neryl/geranyl triphenylphosphonium chloride was prepared by reacting neryl/geranyl chloride with triphenylphosphine in benzene solvent according to the procedure described by Isler et al in *Helvetica Chimica Acta*, 39, page 463 (1956), which is incorporated herein expressly by reference. Both the neryl and geranyl isomers of the phosphonium salt were present. The neryl/geranyl triphenylphosphonium chloride (50 grams) was dissolved in 63 grams of a 20% aqueous solution of hydrogen chloride. This solution was heated at reflux and samples were removed at several intervals during the course of the reaction. The samples were analyzed by NMR analysis. After 12 hours reaction time, the desired beta-cyclogeranyl triphenylphosphonium chloride product was evident from the analysis.

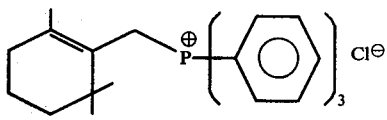

beta-Cyclogeranyl triphenylphosphonium chloride

In order to further confirm the structure of the product, the phosphonium salt was hydrolyzed by the addition of 100 grams of 50% aqueous sodium hydroxide. The hydrolyzed reaction mixture then was steam distilled to remove 9 grams of the volatile hydrolysis product. Gas chromatographic analysis of the hydrolysis product indicated the presence of the following compounds: 36.5% benzene, 50.9% dihydrobeta-pyronene (1,2,3,3-tetramethyl-1-cyclohexene), 10.3% 1-methylene-2,3,3-trimethylcyclohexane, and 1.8% 2,3,4,4-tetramethyl-1-cyclohexene.

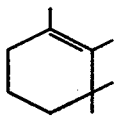 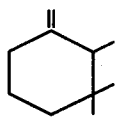

Dihydro-beta-pyronene   1-Methylene-2,3,3-trimethylcyclohexane

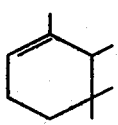

2,3,4,4-Tetramethyl-1-cyclohexene

It should be noted that under anhydrous basic conditions, beta-cyclogeranyl triphenylphosphonium chloride can be converted to the corresponding phosphorane, beta-cyclogeranyl triphenylphosphinylide, as described in *Angewandte Chem. International Edition/Sample Issue*, supra.

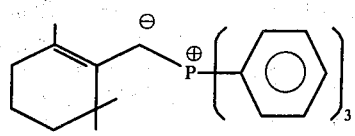

beta-Cyclogeranyl triphenylphosphinylide

We claim:
1. A process for cyclizing an acyclic terpenoid group of an onium salt selected from a quaternary ammonium salt and a phosphonium salt, where said terpenoid group is a neryl group or a geranyl group, which comprises
   maintaining an acidic aqueous solution of said onium salt at a temperature of at least about 80° C. until said acyclic terpenoid group cyclizes, there being at least about 1.1 equivalents of acid per equivalent of said onium salt.
2. The process of claim 1 wherein said temperature is between about 80° and 120° C., and at least about 2 equivalents of acid are used.
3. The process of claim 1 wherein said cycloterpenoid group is an alpha-, beta-, or gamma-cyclogeranyl group, or mixtures thereof.
4. The process of claim 1 wherein said onium salt is a quaternary ammonium halide.
5. The process of claim 1 wherein said onium salt is a phosphonium halide.
6. The process of claim 4 wherein said cycloterpenoid onium halide is rendered basic to form the corresponding cycloterpenoid onium hydroxide.
7. The process of claim 6 wherein said onium halide is rendered basic by treatment with a strong base or basic ion exchange resin.
8. The process of claim 7 wherein said strong base is an alkali metal hydroxide.
9. The process of claim 1 wherein said cycloterpenoid onium salt is a cycloterpenoid quaternary ammonium salt which is thermally decomposed to yield a mixture of gamma-pyronene and delta-pyronene.
10. The process of claim 7 wherein said cycloterpenoid onium hydroxide is thermally decomposed to form a mixture of gamma-pyronene and delta-pyronene.
11. The process of claim 1 wherein said cycloterpenoid onium salt is recovered from said aqueous mixture.
12. The process of claim 9 wherein said gamma-pyronene is recovered, hydroborated under hydroboration conditions, and then treated with an aqueous hydrogen peroxide agent to form alpha-cyclogeraniol.
13. The process of claim 12 wherein said hydroboration is conducted in diglyme solvent with diborane.
14. The process of claim 10 wherein said gamma-pyronene is recovered, hydroborated under hydroboration conditions, and then treated with an aqueous hydrogen peroxide agent to form alpha-cyclogeraniol.
15. The process of claim 14 wherein said hydroboration is conducted with diborane is digylme solvent and said hydrogen peroxide agent is hydrogen peroxide.
16. The process of claim 9 wherein said delta-pyronene is recovered, hydroborated under hydroboration conditions, and then treated with an aqueous hydrogen peroxide agent to form a mixture of 1-hydroxymethyl-2-methylene-3,3-dimethylcyclohexane and 1-methylene-2-hydroxymethyl-3,3-dimethylcyclohexane.
17. The process of claim 16 wherein said hydroboration is conducted with diborane in diglyme.

18. The process of claim 10 where said delta-pyronene is recovered, hydroborated under hydroboration conditions, and then treated with an aqueous hydrogen peroxide agent to form a mixture of 1-hydroxymethyl-2-methylene-3,3-dimethylcyclohexane and 1-methylene-2-hydroxymethyl-3,3-dimethylcyclohexane.

19. The process of claim 18 wherein said hydroboration is conducted with diborane in diglyme.

20. 1-Hydroxymethyl-2-methylene-3,3-dimethylcyclohexane.

21. The process of claim 1 wherein said onium salt reactant has only hydrocarbyl substitution.

22. The process of claim 21 wherein said onium salt is a quaternary ammonium salt.

23. The process of claim 21 wherein said onium salt is a phosphonium salt.

* * * * *

UNITED STATES PATENT AND TRADEMARK OFFICE
CERTIFICATE OF CORRECTION

PATENT NO. : 4,179,468
DATED : Dec. 18, 1979
INVENTOR(S) : Bernard J. Kane and Richard A. Von Genk It is certified that error appears in the above-identified patent and that said Letters Patent are hereby corrected as shown below:

Column 2, line 5, "acylic" should read --acyclic--;
Column 2, line 20, "acrylic" should read --acyclic--.

Signed and Sealed this

Twenty-fourth Day of June 1980

[SEAL]

Attest:

SIDNEY A. DIAMOND

*Attesting Officer*  *Commissioner of Patents and Trademarks*